(12) United States Patent
Hefele et al.

(10) Patent No.: US 6,458,970 B1
(45) Date of Patent: Oct. 1, 2002

(54) METHOD FOR PRODUCING ACID PHTHALIC ANHYDRIDE AND AN APPROPRIATE SHELL CATALYST CONTAINING TITANIUM-VANADIUM-CESIUM

(75) Inventors: Gerhard Hefele, Römerberg; Otto Kratzer, Bobenheim-Roxheim; Walter Scheidmeir, Limburgerhof; Bernhard Ulrich, Bockenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/380,214

(22) PCT Filed: Feb. 12, 1998

(86) PCT No.: PCT/EP98/00779

§ 371 (c)(1),
(2), (4) Date: Aug. 26, 1999

(87) PCT Pub. No.: WO98/37965

PCT Pub. Date: Sep. 3, 1998

(30) Foreign Application Priority Data

Feb. 27, 1997 (DE) .......................... 197 07 943

(51) Int. Cl.$^7$ ............................. C07D 307/89
(52) U.S. Cl. ...................... 549/247; 502/209
(58) Field of Search ................ 549/247; 502/209

(56) References Cited

U.S. PATENT DOCUMENTS

| | | |
|---|---|---|
| 3,871,445 | 3/1975 | Wanka |
| 4,007,136 | 2/1977 | Blechschmitt |
| 4,036,783 | 7/1977 | Blechschmitt |
| 4,046,780 | 9/1977 | Nakanishi |
| 4,077,984 | 3/1978 | Blechschmitt |
| 4,096,094 | 6/1978 | Blechschmitt |
| 4,203,906 | 5/1980 | Takada |
| 4,256,783 | 3/1981 | Takada |
| 4,284,571 | 8/1981 | Sato |
| 4,324,694 | 4/1982 | Reuter |
| 4,356,112 | 10/1982 | Nakanishi |
| 4,481,304 | 11/1984 | Sato |
| 4,879,387 | 11/1989 | Hara |
| 5,169,820 | 12/1992 | Ueda |
| 5,235,071 | 8/1993 | Ueda |

FOREIGN PATENT DOCUMENTS

| | | |
|---|---|---|
| DE | 17 69 998 | 2/1972 |
| DE | 2 201 528 | 11/1972 |
| DE | 24 21 406 | 11/1975 |
| DE | 24 36 009 | 2/1976 |
| DE | 25 10 994 | 9/1976 |
| DE | 25 46 268 | 4/1977 |
| DE | 25 47 624 | 4/1977 |
| DE | 28 30 765 | 1/1980 |
| DE | 29 48 163 | 6/1980 |
| DE | 30 45 624 | 6/1981 |
| EP | 021 325 | 1/1981 |
| EP | 263 231 | 12/1985 |
| EP | 286 448 | 10/1988 |
| EP | 447 267 | 9/1991 |
| EP | 522 871 | 1/1993 |
| EP | 539 878 | 5/1993 |
| GB | 1 496 832 | 1/1978 |

*Primary Examiner*—Paul J. Killos
(74) *Attorney, Agent, or Firm*—Keil & Weinkauf

(57) ABSTRACT

In a process for preparing phthalic anhydride by catalytic gas-phase oxidation of o-xylene or naphthalene or o-xylene/naphthalene mixtures with a gas comprising molecular oxygen over a coated catalyst comprising an inert, nonporous support material on which a catalytically active composition comprising titanium dioxide and vanadium pentoxide is applied in layer form, a catalyst whose catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification is used in the presence or absence of a coated catalyst, differing therefrom, for the catalytic gas-phase oxidation of o-xylene or naphthalene or o-xylene/naphthalene mixtures and, in the presence of such a second catalyst, the latter is used in a combined bed with the catalyst of the above composition in the reactor.

3 Claims, No Drawings

METHOD FOR PRODUCING ACID PHTHALIC ANHYDRIDE AND AN APPROPRIATE SHELL CATALYST CONTAINING TITANIUM-VANADIUM-CESIUM

The present invention relates to a process for preparing phthalic anhydride by catalytic gas-phase oxidation of o-xylene or naphthalene or o-xylene/naphthalene mixtures using a gas comprising molecular oxygen and a coated catalyst comprising an inert, nonporous support material on which a catalytically active composition comprising titanium dioxide and vanadium pentoxide is applied in layer form, and also a catalyst for this purpose.

In the prior art, many catalysts have been proposed for preparing PA from o-xylene or naphthalene or o-xylene/naphthalene mixtures by oxidation with gases comprising molecular oxygen in the gas phase over a fixed-bed catalyst. The PA catalysts generally comprise an inert support material on which a thin layer of the catalytically active composition is applied in the form of a shell, which is why these catalysts are generally also referred to as coated catalysts.

The composition of the catalytically active composition plays a decisive role for the catalytic properties of these PA catalysts. Virtually all PA catalysts employed nowadays have a catalytically active composition comprising the components titanium dioxide, generally in the anatase modification, and vanadium pentoxide. Since PA catalysts whose catalytically active composition consists of these base components alone give economically unsatisfactory results in respect of conversion, yield and selectivity owing to secondary reactions such as the formation of phthalide of the formula

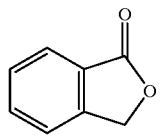

maleic anhydride, benzoic acid and citraconic anhydride of the formula

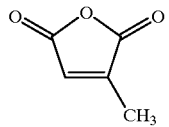

or total combustion and are also not satisfactory in respect of long-term activity and selectivity, the efforts made in the prior art have been directed at improving these catalysts in respect of their activity, selectivity, yield and the quality of the PA product produced therewith by doping the catalytically active composition with a wide variety of additives and ever more additives, ie. increasingly complicated catalyst formulations have been developed over time to solve these problems. Such additives are, for example, antimony, boron, cesium, calcium, cobalt, iron, potassium, lithium, molybdenum, sodium, niobium, phosphorus, rubidium, silver, thalium, bismuth, tungsten and tin.

In DE-A 24 36 009 and DE-A 24 21 406, PA is prepared using coated catalysts which comprise a steatite support and a catalytically active composition comprising from 60 to 99% by weight of titanium dioxide in the anatase modification, from 1 to 40% by weight of vanadium pentoxide and, based on the titanium dioxide, from 0.15 to 1.5% by weight of rubidium and/or cesium.

DE-A 25 10 994 relates to vanadium- and titanium-containing supported catalysts having a particular external shape and whose catalytically active composition can comprise from 70 to 99% by weight of titanium dioxide in the anatase modification having a specific internal surface area of from 5 to 20 m²/g, from 1 to 30% by weight of vanadium pentoxide and up to 5% by weight of other materials such as the oxides of the elements cesium, rubidium, thallium, phosphorus or antimony. No information is given as regards the precise content of these other materials, in particular their ratios to one another. The support material used is steatite (magnesium silicate).

DE-A 25 47 624 describes catalysts for preparing PA, whose catalytically active composition comprises from 60 to 99% by weight of titanium dioxide (anatase), from 1 to 40% by weight of vanadium pentoxide and from 0.1 to 10% by weight of rubidium and antimony in an atomic ratio Rb:Sb of from 1:2.5 to 1:30. The anatase used can, according to this document, have an internal surface area of from 5 to 50 m²/g, preferably from 5 to 20 m²/g; according to an example, anatase having an internal surface area of 11 m²/g is used.

EP-A 21 325 relates to coated catalysts for preparing PA, whose catalytically active composition comprises from 60 to 99% by weight of anatase, from 1 to 40% by weight of vanadium pentoxide and, based on the total amount of TiO₂ and V₂O₅, up to 2% by weight of phosphorus and up to 1.5% by weight of rubidium and/or cesium where the catalytically active composition is applied to the support in two layers, the inner layer of which contains from 0.2 to 2% by weight of phosphorus but no rubidium or cesium and the outer layer of which contains from 0 to 0.2% by weight of phosphorus and from 0.02 to 1.5% by weight of rubidium and/or cesium. The catalytically active composition of these catalysts can, apart from the constituents mentioned, contain small amounts, eg. up to 10% by weight, of an oxide of the metals niobium, tin, silicon, antimony, hafnium, molybdenum or tungsten. The titanium dioxide used for producing these catalysts has an internal surface area of from 5 to 30 m²/g. The support material used is steatite.

EP-A 286 448 relates to a process for preparing PA in which use is made of two types of catalyst in a combined catalyst bed, both of which have similar contents of titanium dioxide and vanadium pentoxide and differ essentially in that one catalyst additionally contains from 2 to 5% by weight of a cesium compound, in particular cesium sulfate, but no phosphorus, tin, antimony, bismuth, tungsten or molybdenum compounds and the second catalyst additionally contains from 0.1 to 3% by weight of a phosphorus, tin, antimony, bismuth, tungsten or molybdenum compound, but virtually no alkali metal.

EP-A 522 871, EP-A 539 878, EP-A 447 267, DE-A 29 48 163 and DE-A 30 45 624 all relate to catalysts for preparing PA which are composed of a porous support material, preferably silicon carbide, and a catalytically active composition comprising, apart from titanium dioxide and vanadium pentoxide, many further catalytically active elements such as phosphorus, alkali metals, antimony (in EP-A 522 871 pentavalent antimony), niobium and/or silver.

Despite progress in catalyst development, the catalysts and catalyst systems known and available at present for the preparation of phthalic anhydride still have a series of disadvantages. The initial PA yield achievable with a fresh catalyst is about 80 mol %, but even in the first year of operation a significant drop in yield has to be accepted. For quality reasons, the phthalic anhydride initially obtained as crude product has to be subjected to a chemical treatment before it can be processed by distillation to give a pure product of the quality required nowadays. Owing to their great sensitivity to temperature, pressure and loading fluctuations, reliable use of these catalysts in large-scale operation requires a high outlay for monitoring and control. A further disadvantage of these catalysts is that, owing to their incomplete o-xylene conversion and the formation of under-oxidized or over-oxidized by-products, they result in odor problems and o-xylene and benzene emissions which, for environmental reasons, make costly waste gas incineration necessary.

These disadvantages are increased at high o-xylene and/or naphthalene loadings of the feed gas stream, in particular at loadings of 80 g of o-xylene per standard $m^3$ of gas and more.

It is an object of the present invention to find a process for preparing PA which does not have the abovementioned disadvantages and to provide a suitable catalyst for this purpose. The process of the invention should, particularly in long-term operation using high o-xylene loadings, continue to give good yields of PA having a high degree of purity and thus make superfluous a chemical work-up of the crude PA to remove disadvantageous by-products which are virtually impossible to remove by distillation, eg. phthalide.

We have found that this object is achieved by a process for preparing phthalic anhydride by catalytic gas-phase oxidation of o-xylene or naphthalene or o-xylene/naphthalene mixtures with a gas comprising molecular oxygen over a coated catalyst comprising an inert, nonporous support material on which a tatalytically active composition comprising titanium dioxide and vanadium pentoxide is applied in layer form, wherein a catalyst whose catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification is used in the presence or absence of a coated catalyst, differing therefrom, for the catalytic gas-phase oxidation of o-xylene or naphthalene or o-xylene/naphthalene mixtures and, in the presence of such a second catalyst, the latter is used in a combined bed with the catalyst of the above composition in the reactor.

We have found that this object is achieved in particular by a process for preparing phthalic anhydride by catalytic gas-phase oxidation of o-xylene or naphthalene or o-xylene/naphthalene mixtures with a gas comprising molecular oxygen over a coated catalyst comprising an inert, nonporous support material on which a catalytically active composition comprising titanium dioxide and vanadium pentoxide is applied in layer form, wherein the coated catalyst used in a first reaction zone nearest the gas inlet into the reactor is one whose catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification and the coated catalyst used in a second reaction zone nearest the outlet for the reaction gases from the reactor is one whose catalytically active composition comprises from 1 to 10% by weight of vanadium pentoxide, calculated as $V_2O_5$, from 0 to 10% by weight of antimony oxide, calculated as $Sb_2O_3$, from 0.01 to 0.3% by weight of a cesium and/or rubidium compound, calculated as Cs or Rb, from 0.01 to 0.3% by weight of a phosphorus compound, calculated as P, and the remainder to 100% by weight of titanium dioxide in the anatase modification.

Furthermore, we have found a catalyst comprising a thin layer of catalytically active components applied in the form of a shell to a nonporous support material, wherein the catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification.

The novel catalyst can be used in the novel process alone or, preferably, in a combined bed with a second catalyst differing therefrom or a plurality of catalysts differing therefrom. Preferably, the novel catalyst is used in a combined bed with a second catalyst, in particular with a second catalyst of the composition described above.

The process of the present invention is thus preferably carried out using a combined catalyst bed, ie. the two catalysts used according to the present invention are arranged above one another in a fixed bed in the individual reaction tubes of the PA reactor in such a way that the first catalyst is nearest the gas inlet for the feed gas stream into the reactor, while the second catalyst is nearest the gas outlet for the reaction gases from the reactor. Since the reaction of the aromatic hydrocarbons takes place in the catalyst bed, the section of the reaction tube or tubes filled with the catalysts in question is also referred to as the reaction zone and the sections of the reaction zone filled with the first and second catalysts are also referred to as the first and second reaction zones respectively. Depending on the type of PA catalysts used according to the present invention, the proportion by volume of said reaction zone occupied by the first reaction zone can be from 25 to 75% by volume, preferably from 50 to 70% by volume.

In the first reaction zone, use is advantageously made according to the present invention of a coated catalyst which comprises an inert, nonporous support material which is heat-resistant under the conditions of PA production on which there is applied a shell-like layer of the catalytically active composition which comprises, based on the weight of this catalytically active composition in the finished catalyst, generally from 3 to 6% by weight, preferably from 3 to 5% by weight and particularly preferably from 3.5 to 4.5% by weight, of vanadium pentoxide, calculated as $V_2O_5$, as well as generally from 0.3 to 0.5% by weight, preferably from 0.35 to 0.45% by weight, of a cesium compound, calculated as Cs, and the remainder to 100% by weight of the catalytically active composition is titanium dioxide in its anatase modification. Since the form (compound or compounds) in which the cesium is present in the finished catalyst is not known, the content of cesium compounds is calculated as Cs.

This composition as stated includes the components deliberately added to produce the catalytically active composition, but any elements present as technically unavoidable impurities in the starting or precursor compounds have not been taken into account, since they were not analyzed for each constituent nor in each experiment.

As inert, nonporous support material which is heat-resistant under the conditions of PA production, the catalyst can comprise sintered or fused silicates, eg. steatite (magnesium silicate), porcelain, alumina, nonporous silicon carbide, rutile or quartz. The support material in the catalyst used according to the present invention is preferably steatite. For coating with the catalytically active composition, the support material can, for example, have the shape of spheres, cylinders, spirals or rings, preference being given to using a support in the form of rings as described in DE-A 25 10 994. In the finished catalyst, the catalytically active composition generally makes up a proportion of from 8 to 12% by weight, preferably from 9 to 11% by weight and particularly preferably from 9.5 to 10.5% by weight, of the total weight of the catalyst. In the present application, the term "finished catalyst" refers to the ready-to-use catalyst which has been coated with the catalytically active composition and possibly heat-treated to convert precursor compounds of the catalytically active components into these catalytically active components and to remove organic auxiliaries for catalyst production.

To produce the catalyst to be employed according to the present invention, the titanium dioxide used is in the anatase modification and generally has a BET surface area of from 13 to 28 $m^2/g$, particularly preferably from 19 to 21 $m^2/g$, and a particle size of generally from 0.12 to 1 μm, preferably from 0.4 to 0.8 μm.

The catalyst to be used according to the present invention in the second reaction zone is different from the catalyst of the first reaction zone. Particular preference is given to using a catalyst in the second reaction zone whose catalytically active composition comprises, based on the total weight of the catalytically active composition in the finished catalyst, generally from 1 to 10% by weight, preferably from 2 to 9% by weight and particularly preferably from 3 to 8% by weight, of vanadium pentoxide, calculated as $V_2O_5$, generally from 0 to 10% by weight, preferably from 0 to 5% by weight and particularly preferably from 0 to 4% by weight, of antimony oxide, calculated as $Sb_2O_3$, generally from 0.01 to 0.3% by weight, preferably from 0.05 to 0.3% by weight and particularly preferably from 0.1 to 0.25% by weight, of a cesium and/or rubidium compound, calculated as Cs or Rb, and also generally from 0.01 to 0.3% by weight, preferably from 0.05 to 0.3% by weight and particularly preferably from 0.1 to 0.25% by weight, of a phosphorus compound, calculated as P. The content of a phosphorus compound in the catalyst is calculated as P, since the form (compound or compounds) in which the phosphorus compound or compounds added during catalyst production is/are present in the finished catalyst is not known.

Of course, other catalysts suitable for oxidizing aromatic hydrocarbons and having a composition differing from the above composition may also be used in the second reaction zone, for example with [sic] commercially available catalysts or catalysts as described, for example, in DE-A 25 46 268, EP-A 286 448, DE-A 25 47 624, DE-A 29 48 163, EP-A 163 231, DE-A 28 30 765, DE-A 17 69 998, EP-A 522 871, EP-A 539 878, EP-A 447 267, DE-A 30 45 624 or DE-A 40 13 051.

The information regarding the support material, the type of titanium dioxide to be used for the catalytically active composition and the proportion by weight of the catalytically active composition in the total catalyst given in the explanation of the catalyst advantageously to be used according to the present invention in the first reaction zone also applies to the catalyst advantageously to be used according to the present invention in the second reaction zone.

In accordance with the above statements on the composition of the catalyst preferably to be used in the second reaction zone, antimony may be present or absent in this catalyst. The antimony oxide may be present in these catalysts as, for example, $Sb_2O_3$, $Sb_2O_4$ or $Sb_2O_5$; preference is given to using $Sb_2O_3$ for producing the catalyst.

The statements regarding to the composition of the catalyst preferably used in the second reaction zone indicate the element components which are deliberately used for producing the catalytically active composition. Any technically unavoidable impurities present in the starting materials for producing the catalytically active composition have not been taken into account in the statements, since they were not analyzed for each constituent nor in each experiment.

The catalysts advantageously to be employed according to the present invention in the two reaction zones can be produced in a manner which is conventional per se by applying the catalytically active composition or the precursor compounds of the catalytically active components present in the catalytically active composition to the support, for example as described in DE-A 25 10 994 by spraying a mix comprising the components of the catalytically active composition or their precursor compounds onto the support preheated, for example, to from 100 to 450° C., for example in a coating drum. The catalytically active composition can also be applied to the support material by methods other than spraying, eg. by application of a paste-like mass comprising the catalytically active components or their precursor compounds and also auxiliaries for catalyst production to the support, eg. in a coating drum, or by application of a powder which has been preprepared by, for example, spray or freeze drying and comprises the catalytically active components and/or their precursor compounds to the support material, eg. in a coating drum, with a small amount of a solvent being sprayed into the coating apparatus during the coating process to aid the adhesion of the powder to the preheated support, subsequent drying and possibly calcination at up to 450° C., preferably up to 400° C.

To prepare the mix or the paste-like composition, the catalytically active components of the catalyst or their precursor compounds, for example in the form of their oxides, salts, nitrates, $C_1$–$C_{10}$-carboxylates, carbonates, hydrogencarbonates, sulfates, hydrogensulfates, halides or phosphates or as complexes, for example as oxalate or acetylacetone complexes, and also any auxiliaries used for catalyst production are dissolved, or if an individual material is not soluble, suspended in a solvent. Solvents or suspension media which can be used are water or organic liquids or mixtures of water with these liquids. Preference is given to using water or water in admixture with organic liquids, where the mixing ratio of water/organic liquid is generally not critical but preference is given to using those solvent mixtures containing 50 or more percent by weight of water.

As organic liquids, preference is given to using water-soluble solvents such as $C_1$–$C_4$-alcohols, water-soluble ethers, eg. tetrahydrofuran, dioxane or ethylene glycol dimethyl ether, water-soluble amides, eg. formamide, pyrrolidone, N-methylpyrrolidone or N,N-dimethylformamide, or water-soluble sulfoxides, eg. dimethyl sulfoxide.

Auxiliaries for catalyst production which can be added to the mix or paste-like mass are binders, pore formers and/or temporary activity damping agents.

For the purposes of the present invention, the term binder refers to a substance which permanently or temporarily improves the adhesion of the individual particles of the catalytically active composition or the precursor compounds thereof to one another and/or to the support material. Examples of binders which can be used for producing the catalysts to be used according to the present invention are polyols such as ethylene glycol, propylene glycol, butylene glycols or glycerol or amides such as formamide, N,N-dimethylformamide, N,N-diethylformamide, N,N-dibutylformamide, acetamide, pyrrolidone or N-methylpyrrolidone.

The term pore former is used hereinafter to describe a substance which, by means of a volume change, for example by vaporization or decomposition during the heat treatment to generate the catalytically active metal oxides from their precursor compounds, effects, during the production of the coated catalyst, the formation in the active composition of a pore structure which is changed from that in an active composition to which no pore former has been added during its production. Pore formers which can be used in the process of the present invention are, for example, polyols such as glycerol or polymers such as cellulose, methylcellulose, cellulose acetate or starch, or acids such as oxalic acid, tartaric acid or lactic acid, or else amines such as melamine or amides such as urea. The type and amount of the auxiliaries to be added generally depends on the chemical composition of the catalytically active composition of the coated catalyst in question and the starting materials used and is advantageously optimized in a preliminary experiment for the catalytically active composition having a particular chemical composition to be produced in each case.

For the purposes of the present invention, the term temporary activity damping agents refers to the abovementioned binders or ore formers or else to all further auxiliaries which, for a limited period, lead to a reduction in activity and/or a lowering of the hot spot temperature and thus aid the running-up of the reactor or the increase in loading to full-load operation of the reactor without reducing the mean catalytic activity or selectivity.

The catalysts produced in this way are preferably used for the gas-phase oxidation of o-xylene or naphthalene or o-xylene/naphthalene mixtures to give phthalic anhydride.

For this purpose, the catalysts to be employed according to the present invention are introduced into the reaction tubes which are then advantageously thermostated from the outside, for example by means of a salt bath, to the reaction temperature. The reaction gas is then passed over the catalyst bed thus prepared generally at from 300 to 450° C., preferably from 320 to 420° C. and particularly preferably from 340 to 400° C. and at a gauge pressure of generally from 0.1 to 2.5 bar, preferably from 0.3 to 1.5 bar, at a space velocity of generally from 750 to 5000 $h^{-1}$.

The reaction gas fed to the catalyst is generally produced by mixing a gas comprising molecular oxygen, preferably air, which gas can comprise not only oxygen but also suitable reaction moderators and/or diluents such as steam, carbon dioxide and/or nitrogen, with the aromatic hydrocarbon to be oxidized; the gas comprising molecular oxygen can comprise generally from 1 to 100% by volume, preferably from 2 to 50% by volume and particularly preferably from 10 to 30% by volume, of oxygen, from 0 to 30% by volume, preferably from 0 to 10% by volume, of water vapor and also from 0 to 50% by volume, preferably from 0 to 1% by volume, of carbon dioxide, remainder nitrogen. To produce the reaction gas, the aromatic hydrocarbon to be oxidized is introduced into the gas comprising molecular oxygen in an amount of generally from 40 g to 140 g per standard $m^3$ of gas, preferably from 60 to 120 g per standard $m^3$ of gas and particularly preferably from 80 to 115 g per standard $m^3$ of gas.

The gas-phase oxidation can advantageously be carried out with two or more zones, preferably two zones, of the catalyst bed present in the reaction tube being thermostated to different reaction temperatures, for which purpose it is possible to use, for example, reactors having separate salt baths as are described, for example, in DE-A 22 01 528 or DE-A 28 30 765. It is possible here, as described in DE-A 40 13 051, to thermostat the reaction zone nearest the gas inlet for the feed gas, which zone generally makes up, as already mentioned, from 25 to 75% by volume of the total reactor volume, to a reaction temperature which is from 1 to 20° C., preferably from 1 to 10° C. and in particular from 2 to 8° C., higher than that in the reaction zone nearest the gas outlet. Alternatively, the gas-phase oxidation can also be carried out at the same reaction temperature in both reaction zones without division into temperature zones.

In general, the reaction is controlled by setting the temperature of the salt bath in such a way that the major part of the aromatic hydrocarbon present in the feed gas is reacted with maximum yield in the first zone. The aromatic hydrocarbon is preferably reacted virtually completely with maximum yield in the first reaction zone.

The process of the present invention avoids, as demonstrated by the following examples, the disadvantages of the PA processes and catalysts of the prior art, even at high o-xylene and/or naphthalene loadings in the feed gas stream of 80 g/standard $m^3$ of gas and higher. This is particularly surprising since the catalysts to be employed according to the present invention have a relatively simple composition and the catalyst of the first reaction zone has a very low vanadium oxide content compared with other catalysts of the prior art.

EXAMPLES

In all examples of catalyst production, the BET surface area was determined by the method of Brunauer et al, J. Am. Chem. Soc. 60 (1938), 309.

Example 1

Production of the Catalyst I 700 g of steatite rings having an external diameter of 8 mm, a length of 6 mm and a wall thickness of 1.5 mm were heated to 160° C. in a coating drum and sprayed with a suspension of 400 g of anatase (analysis: Ti: 59.5% by weight; S: 0.18% by weight; P: 0.08% by weight; Nb: 0.32% by weight; K: 0.007% by weight; Na: 0.04% by weight; Fe: 0.002% by weight; Zr: 0.003% by weight; Pb: 0.003% by weight; W: 0.02% by weight) having a BET surface area of 21 $m^2$/g, 30.7 g of vanadyl oxalate, 2.60 g of cesium sulfate, 618 g of water and 128 g of formamide until the weight of the layer applied corresponded to 10.5% of the total weight of the finished catalyst. The catalytically active composition applied in this way ie. the catalyst shell, contained 4% by weight of vanadium (calculated as $V_2O_5$), 0.4% by weight of cesium (calculated as Cs) and 95.6% by weight of titanium dioxide.

Example 2

Production of the Catalyst II 700 g of steatite rings having an external diameter of 8 mm, a length of 6 mm and a wall thickness of 1.5 mm were heated to 180° C. in a coating drum and sprayed with a suspension of 400 g of anatase (analysis: Ti: 59.5% by weight; S: 0.18% by weight; P: 0.08% by weight; Nb: 0.32% by weight; K: 0.007% by weight; Na: 0.04% by weight; Fe: 0.002% by weight; Zr: 0.003% by weight; Pb: 0.003% by weight; W: 0.02% by weight) having a BET surface area of 21 $m^2$/g, 57.6 g of vanadyl oxalate, 14.4 g of antimony trioxide, 2.5 g of ammonium hydrogen phosphate, 0.65 g of cesium sulfate, 618 g of water and 128 g of formamide until the weight of the layer applied corresponded to 10.5% of the total weight of the finished catalyst. The catalytically active composition applied in this way, ie. the catalyst shell, contained 0.15% by weight of phosphorus (calculated as P), 7.5% of vanadium (calculated as $V_2O_5$), 3.2% by weight of antimony (calculated as $Sb_2O_3$), 0.1% by weight of cesium (calculated as Cs) and 88.75% by weight of titanium dioxide.

Example 3

Production of the Catalyst III 700 g of steatite rings having an external diameter of 8 mm, a length of 6 mm and a wall thickness of 1.5 mm were heated to 160° C. in a coating drum and sprayed with a suspension of 400 g of anatase having a BET surface area of 21 m²/g, 30.7 g of vanadyl oxalate, 3.33 g of ammonium hydrogen phosphate, 2.60 g of cesium sulfate, 618 g of water and 128 g of formamide until the weight of the layer applied corresponded to 10.5% of the total weight of the finished catalyst. The catalytically active composition applied in this way, ie. the catalyst shell, contained 4.0% by weight of vanadium (calculated as $V_2O_5$), 0.2% by weight of cesium (calculated as Cs), 0.2% by weight of phosphorus (calculated as P) and 95.4% by weight of titanium dioxide.

Example 4

Catalyst System A

Catalyst I was used in the first reaction zone and the catalyst used in the second reaction zone was catalyst II whose catalytically active composition had the following chemical composition in percent by weight, based on the weight of the catalytically active composition in the finished catalyst:

|  | Catalyst I | Catalyst II |
|---|---|---|
| $V_2O_5$ | 4.0 | 7.5 |
| $Sb_2O_3$ | — | 3.2 |
| Cs | 0.4 | 0.1 |
| Phosphorus (P) | — | 0.15 |
| Remainder | Anatase | Anatase |

The lower part of a steel reaction tube having a length of 3.5 m and an internal diameter of 25 mm was charged with catalyst II and the part above that was charged with catalyst I. The fill height of the catalyst II was 130 cm and that of the catalyst I was 160 cm. The upper 50 cm of the reaction tube at the gas inlet was free of catalyst. The reaction tube was thermostated using a liquid heat transfer medium (salt bath) via which the heat of reaction was also removed.

The catalyst support consisted of cylindrical rings having the dimensions 6 mm (height), 8 mm (external diameter) and 5 mm (internal diameter).

4 m³/h of air were passed from the top downward through the reaction tube, with the o-xylene loading being 95 g/m³ of air. The purity of the o-xylene was 98.2%. At a salt bath temperature of 350° C., the hot spot temperature in the catalyst bed reached from 430 to 440° C. The hot spot was located at a depth of from about 40 to 60 cm in the first reaction zone.

The organic constituents of the reaction gas leaving the reaction tube comprised 95.8% by weight of phthalic anhydride. Significant by-products were maleic anhydride (3.2% by weight), benzoic acid (0.51% by weight), phthalide (0.07 by weight) and citraconic anhydride (0.34% by weight).

The amount of PA formed was 435 g/h, corresponding to a PA yield of 83.5 mol % based on 100%-pure o-xylene. The crude PA condensed from the reaction gas was able to be worked up in a 2-stage vacuum distillation without problems and without pretreatment, to give a pure PA having a purity of 99.9% according to GC. The melt color number was from 5 to 10 (APHA) and the heat color number (90 minutes at 250° C.) was from 10 to 20 (APHA).

After the catalyst had been in operation for one year, the PA yield was still 82.7 mol %.

The environmentally critical materials o-xylene and benzene were present in the reaction gas in amounts of 31 mg/M³ and 2.5 mg/m3 respectively. Owing to their low concentration, these materials did not need to be removed from or depleted in the waste gas.

Example 5

Catalyst System B

Catalyst I was used in the first reaction zone and the catalyst used in the second reaction zone was catalyst III whose catalytically active composition had the following chemical composition in percent by weight, based on the weight of the catalytically active composition in the finished catalyst:

|  | Catalyst I | Catalyst III |
|---|---|---|
| $V_2O_5$ | 4.0 | 4.0 |
| Cs | 0.4 | 0.2 |
| Phosphorus (P) | — | 0.2 |
| Remainder | Anatase | Anatase |

The lower part of a steel reaction tube having a length of 3.5 m and an internal diameter of 25 mm was charged with catalyst III and the part above that was charged with catalyst I. The fill height of the catalyst III was 130 cm and that of the catalyst I was 170 cm. The upper 40 cm of the reaction tube at the gas inlet was empty.

The reaction tube was thermostated using a liquid heat transfer medium (salt bath) via which the heat of reaction was also removed.

The catalyst support consisted of cylindrical rings having the dimensions 6.5 mm (height), 7 mm (external diameter) and 4 mm (internal diameter).

4 m³/h of air were passed from the top downward through the reaction tube. The o-xylene loading of the air was 85 g/m³ and the purity of the o-xylene was 98.2%. At a salt bath temperature of 355° C., the hot spot temperature reached from 435 to 445° C. The hot spot was located at a depth of from about 60 to 70 cm in the first reaction zone.

The organic constituents of the reaction gas leaving the reaction tube comprised 95.9% by weight of phthalic anhydride. Significant by-products were maleic anhydride (2.87% by weight), benzoic acid (0.49% by weight), phthalide (0.18% by weight) and citraconic anhydride (0.35% by weight).

388 g/h of PA were formed, corresponding to a PA yield of 83.2 mol %, based on 100%-pure o-xylene. The crude PA obtained from the reaction gas was able to be worked up in a 2-stage vacuum distillation without problems and without pretreatment to give pure PA having a purity of 99.9% according to GC. The melt color number of the pure product was from 5 to 10 (APHA), and the heat color number (90 minutes at 250° C.) was 20 (APHA).

After the catalyst had been operating for 10 months, the PA yield was still 82.8 mol %.

The environmentally problematical materials o-xylene and benzene were present in comparable concentrations to those described in Example 4. Reduction of the concentrations in the waste gas was not necessary here either.

We claim:

1. A process for preparing phthalic anhydride by catalytic gas-phase oxidation of o-xylene or naphthalene or o-xylene/naphthalene mixtures with a gas comprising molecular oxygen over a coated catalyst comprising an inert, nonporous support material on which a catalytically active composition comprising titanium dioxide and vanadium pentoxide is applied in layer form, wherein a catalyst whose catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification is used in the presence or absence of a coated catalyst, differing therefrom, for the catalytic gas-phase oxidation of o-xylene or naphthalene or o-xylene/naphthalene mixtures and, in the presence of such a second catalyst, the latter is used in a combined bed with the catalyst of the above composition in the reactor.

2. A process as claimed in claim 1, wherein the coated catalyst used in a first reaction zone nearest the gas inlet into the reactor is one whose catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification and the coated catalyst used in a second reaction zone nearest the outlet for the reaction gases from the reactor is one whose catalytically active composition comprises from 1 to 10% by weight of vanadium pentoxide, calculated as $V_2O_5$, from 0 to 10% by weight of antimony oxide, calculated as $Sb_2O_3$, from 0.01 to 0.3% by weight of a cesium and/or rubidium compound, calculated as Cs or Rb, from 0.01 to 0.3% by weight of a phosphorus compound, calculated as P, and the remainder to 100% by weight of titanium dioxide in the anatase modification.

3. A catalyst comprising a thin layer of catalytically active components applied in the form of a shell to a nonporous support material, wherein the catalytically active composition comprises from 3 to 6% by weight of vanadium pentoxide, calculated as $V_2O_5$, from 0.3 to 0.5% by weight of a cesium compound, calculated as Cs, and the remainder to 100% by weight of titanium dioxide in the anatase modification.

* * * * *